United States Patent
Ravindran

(10) Patent No.: US 8,498,424 B2
(45) Date of Patent: Jul. 30, 2013

(54) METHOD AND APPARATUS FOR AN ADAPTIVE GAIN CONTROL UNIT

(75) Inventor: Sourabh Ravindran, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 843 days.

(21) Appl. No.: 12/511,734

(22) Filed: Jul. 29, 2009

(65) Prior Publication Data
US 2010/0027802 A1     Feb. 4, 2010

Related U.S. Application Data

(60) Provisional application No. 61/085,524, filed on Aug. 1, 2008.

(51) Int. Cl.
*A61B 7/04* (2006.01)

(52) U.S. Cl.
USPC .............................................. 381/67; 381/106

(58) Field of Classification Search
USPC ................... 381/103, 67, 104–109
See application file for complete search history.

(56) References Cited

U.S. PATENT DOCUMENTS

| | | | |
|---|---|---|---|
| 5,610,987 A | 3/1997 | Harley | |
| 6,359,992 B1* | 3/2002 | Preves et al. | 381/312 |
| 6,442,279 B1* | 8/2002 | Preves et al. | 381/72 |
| 7,006,638 B1 | 2/2006 | Baekgaard et al. | |
| 2006/0078140 A1* | 4/2006 | Goldstein | 381/312 |
| 2008/0232604 A1* | 9/2008 | Dufresne et al. | 381/67 |

OTHER PUBLICATIONS

"The Embedded Digital Stethoscope Uses the Adaptive Noise Cancellation Filter and the Type I Chebyshev IIR Bandpass Filter to Reduce the Noise of the Heart Sound," IEEE International Workshop on Enterprise Networking and Computing in Healthcare Industry, 2005, pp. 278-281 (Ying-Wen Bai and Chao-Lin Lu).

"Sensor System for Heart Sound Biomonitor," Elsevier Micoelectronics Journal 31 (2000), pp. 583-592 (L.T. Hall, J.L. Maple, J. Agzarian and D. Abbott).

"Model Based Development of a Hearing Aid," M.S. Thesis, Brigham Young University, Provo, Utah, 1994, pp. 1-83 (David V. Anderson).

Application of a Human Auditory Model to Loudness Perception and Hearing, Proceedings of the IEEE International Conference on Acoustics, Speech and Signal Processing, May 1995, pp. 1-4 (Douglas M. Chabries, David V. Anderson, Thomas G. Stockham Jr. and Richard W. Christiansen).

* cited by examiner

*Primary Examiner* — Disler Paul
(74) *Attorney, Agent, or Firm* — Mirna Abyad; W. James Brady; Frederick J. Telecky, Jr.

(57) ABSTRACT

A method and apparatus of an adaptive gain control (AGC) unit. The method includes receiving a noisy input signal and determining to utilize a stethoscope in at least one of a noise suppression mode or in amplification mode depending if the noise level is at least one of above or below a threshold, wherein the stethoscope is in noise suppression mode when K is less than the threshold and is amplification mode when K is above the threshold.

9 Claims, 5 Drawing Sheets

METHOD AND APPARATUS FOR AN ADAPTIVE GAIN CONTROL UNIT

CROSS-REFERENCE TO RELATED APPLICATIONS

This application claims benefit of U.S. provisional patent application Ser. No. 61/085,524, filed Aug. 1, 2008, which is herein incorporated by reference.

BACKGROUND OF THE INVENTION

1. Field of the Invention

Embodiments of the present invention generally relate to a method and apparatus for an adaptive gain control Unit, and more specifically, a gain adaptation and noise suppression for a stethoscope.

2. Description of the Related Art

Stethoscopes that incorporate a digital signal processor to process signal recorded by a stethoscope sensor before conveying the processed signal to the user, are gaining popularity. The advantage of using the digital signal processor is the ability to provide amplification and noise reduction, along with visualization and other signal analysis abilities.

Active noise removal in digital stethoscopes is accomplished by using 2 or more additional sensors to pick up the ambient noise and using an adaptive filtering algorithm to remove the noise from the signal picked up by the main sensor. The issue with such an approach, apart from the need for multiple sensors, is that it could introduce musical noise artifacts in the noise suppressed signal.

Another approach to removing noise is the use of wavelet de-noising. Such an approach may, due to the similarity between the time-domain shape of the heart sound and the shape of the wavelets, facilitate coding the waveform into the wavelet domain using only a few coefficients, and then, reconstruct the waveform to remove noise.

These solutions provide linear amplification, rather than adaptive gain. The level of amplification may be set by the user. As such, most current digital stethoscopes provide a linear amplification, as opposed to adaptive gain, that could lead to saturation and clipping of the waveform, if the signal intensity were to increase. Other solutions use a digital signal processor to perform automatic control of amplification and adaptively removing noise. However, such solutions use different methods to achieve different functionality.

Therefore, there is a need for a method and/or apparatus that would for improving the functionality of a digital stethoscope, while utilizing a single method and the same system.

SUMMARY OF THE INVENTION

Embodiments of the present invention relate to a method and apparatus of an adaptive gain control (AGC) unit. The method includes receiving a noisy input signal and determining to utilize a stethoscope in at least one of a noise suppression mode or in amplification mode depending if the noise level is at least one of above or below a threshold, wherein the stethoscope is in noise suppression mode when K is less than the threshold and is amplification mode when K is above the threshold.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. Herein, a computer readable medium is any medium utilized by a computer for reading, writing, storing, archiving, executing, and the like data or computer instruction.

DETAILED DESCRIPTION

Figure 1:
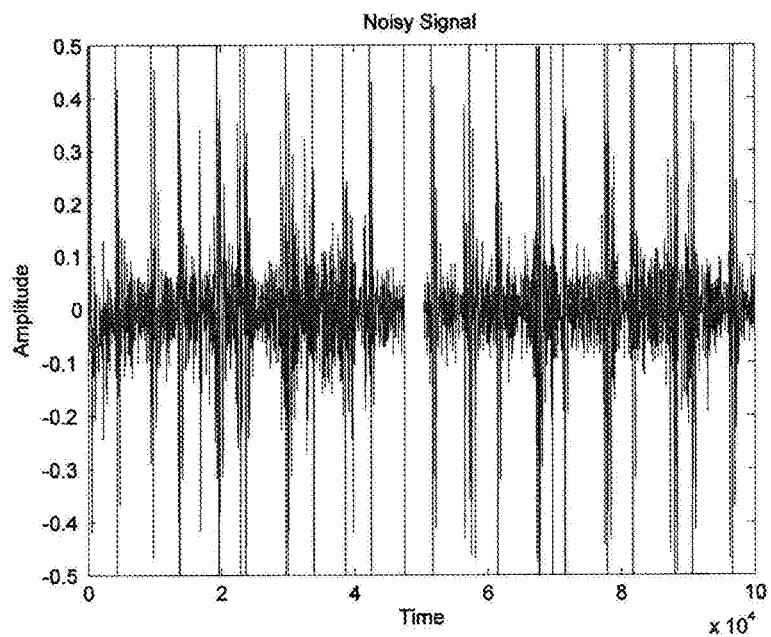
FIG. 1 is an embodiment depicting noisy input signal.

The proposed stethoscope method is computationally inexpensive and does not introduce any musical noise artifacts compared to the other active noise removal techniques currently used in digital stethoscopes. Also the same algorithm can be used to provide time-varying gain control, dynamic range compression or selective boosting of primary heart sounds or murmurs during analysis of the stored heart sounds. The stethoscope method converts a time-varying adaptive gain control system to a noise suppression system. Unlike the adaptive noise cancellation approaches, the proposed stethoscope method does not need to have additional sensors to estimate noise and perform the suppression.

Time-varying gain adaptation is the process of providing non-linear gain to a signal based on its relative amplitude. It is desirable to boost the low amplitude portions of the signal to aid in better hearing. A digital signal processor in conjunction with a stethoscope is used to provide time-varying gain to the recorded signal. In the presence of ambient noise, the same system may be used to suppress noise, while preserving the primary heart sounds.

Such a stethoscope system may be used to provide gain to murmurs present in the recorded or real time signal, so that they are more audible. The proposed system may be couple with a larger system, such as, a wireless network, which has a lower dynamic range. In such an embodiment, the proposed system may be used to change the dynamic range of signal to suit the need.

The stethoscope system comprises a sensor to pickup the audio signal, an ADC to convert the analog signal to a digital signal, a digital signal processor, a DAC, speakers and a channel to deliver the audio to the speakers. The analog input signal is converted to a digital signal by the ADC and conveyed to the digital signal processor, the digital signal processor implements the time-varying gain adaptation algorithm to provide the selected functionality from amongst the above mentioned functionalities.

Given a noisy signal a common approach is to use a Wiener filter to suppress the noise. The solution to the Wiener filtering problem can be approximately expressed as, $$W(f)=SNR(f)/(SNR(f)+1) \qquad \text{(b 1)}$$

where, W(f) is the frequency response of the Wiener filter. It is clear that the Wiener filter provides a near unity gain at high SNRs and a low gain at low SNRs, thereby suppressing the effects of noise.

We approach the problem from a slightly different perspective, namely that of adaptive gain control and achieve a similar functionality as that of the Wiener gain function.

For the Adaptive Gain Compression, an acoustic signal can be expressed as, $$s(t) = \Sigma_i m_i(t) v_i(t)$$

where $v_i(t)$ is the carrier and $m_i(t)$ is the message signal in the $i^{th}$ channel. The relationship between the non-linearly compressed envelope and the original envelope can be expressed as, $$n_i(t) = \beta\, m_i(t)^\alpha \quad (2)$$

$$n_i(t) = G\, m_i(t) \quad (3)$$

where $G = \beta\, m_i^{(\alpha-1)}(t)$. Equation [2] can be re-written as, $$\log(n_i(t)) = \alpha \log(m_i(t)) + \log \beta \quad (4)$$

$\alpha$ and $\beta$ are computed based on the desired range of compressed envelope.

The gain function may be designed such that the maximum of the input corresponds to unity gain. The minimum of the compressed envelope is chosen to be a scaled version of the minimum of the input envelope.

$$n_{i\,max} = m_{i\,max} \quad (5)$$

$$n_{i\,min} = K\, m_{i\,min} \quad (6)$$

where K is a positive scaling factor. Using Eqn. (5) in (4), $$\log(m_{i\,max}) = \alpha \log(m_{i\,max}) + \log(\beta)$$

$$\log(\beta) = (1-\alpha)\log(m_{i\,max}) \quad (7)$$

$$\beta = m_{i\,max}^{1-\alpha} \quad (8)$$

using (6) in (4) and substituting for $\log(\beta)$, $$\log(Km_{i\,min}) = \alpha \log(m_{i\,min}) + \log(\beta)$$

$$(1-\alpha)\log(m_{i\,min}) + \log(K) = (1-\alpha)\log(m_{i\,max})$$

$$(1-\alpha)\log(m_{i\,min}/m_{i\,max}) = -\log(K)$$

$$\alpha = 1 - \log(K)/\log(M) \quad (9)$$

where, $M = m_{i\,min}/m_{i\,max}$

The gain function multiplying the signal is given by, $$G = \beta\, m_i^{(\alpha-1)}$$

$$G = (m_{i\,max})^P m^{-P}$$

$$G = (m_{i\,max}/m)^P \quad (10)$$

where $P = \log(K)/\{\log(M)$. Since $M \leq 1$, $$G \geq 1 \text{ when } K \geq 1$$

$$< 1 \text{ when } K < 1$$

Low-SNR conditions are set to $0 \leq K < 1$ and high-SNR/clean conditions are set to be $K \geq 1$, wherein 1 is the selected threshold. For noise Suppression, as described above, by setting the value of K<1, wherein 1 is the selected threshold, parts of the signal that correspond to noise are suppressed.

Figure 2:
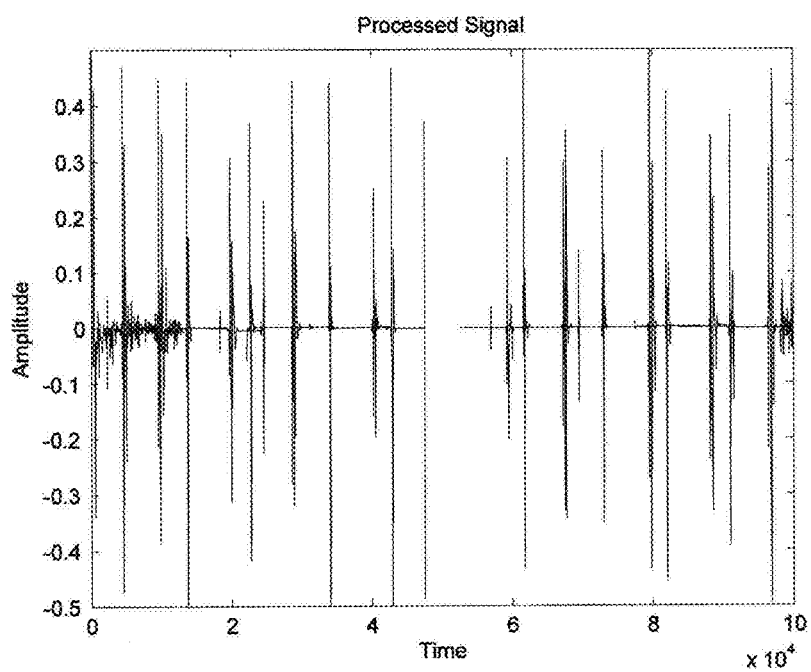
FIG. 2 is an embodiment depicting results for stethoscope method and apparatus with K=0.001.

FIG. 1 is an embodiment depicting noisy input signal. FIG. 2 is an embodiment depicting results for stethoscope method and apparatus with K=0.001. The signal shown in FIG. 1 is introduced to the stethoscope method and apparatus resulting in the signal presented in FIG. 2. As shown in FIG. 2, the S1 and S2 locations are preserved while noise is suppressed.

Figure 3:
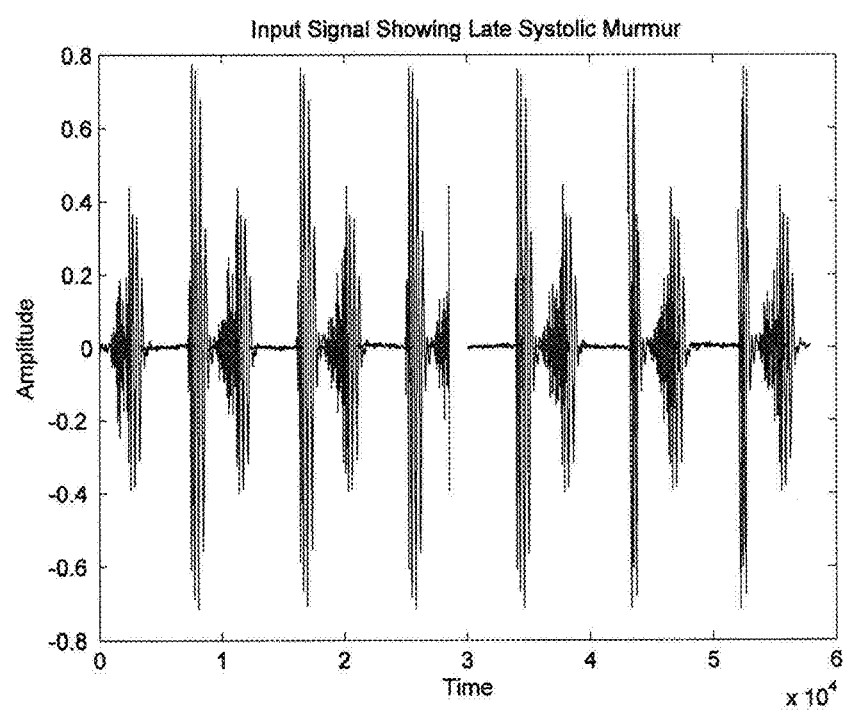
FIG. 3 is an embodiment of an input signal prior to boosting.
Figure 4:
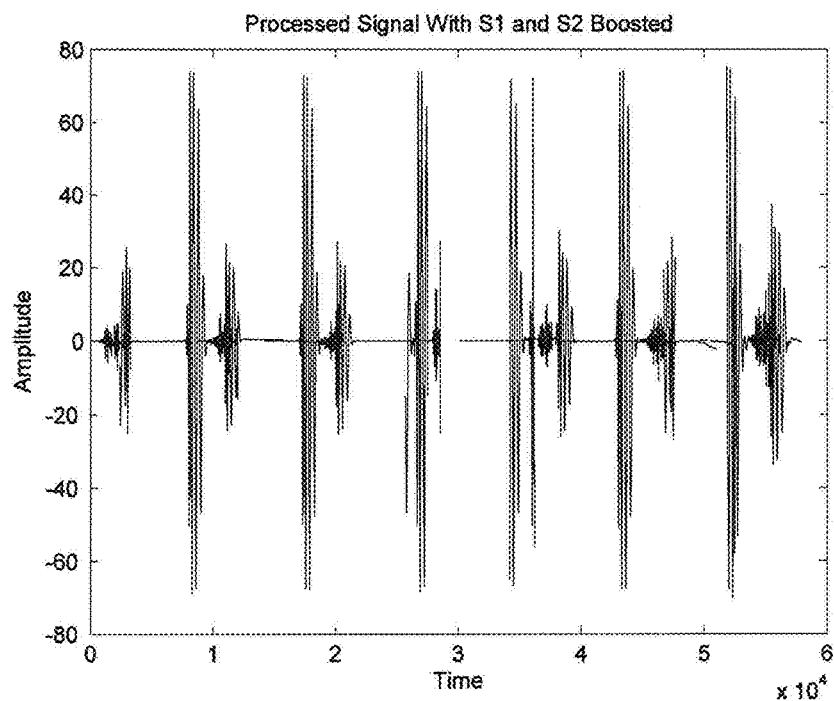
FIG. 4 is an embodiment depicting process signal, after a boost, with $k_1=100$ and $k_2=1$.

In order to boost a primary heart sounds, a method utilizing equations 5 and 6, are rewriting as follows:

$$n_{i\,max} = k_1\, m_{i\,max}$$

$$n_{i\,min} = k_2\, m_{i\,min}$$

where, $k_1$ and $k_2$ can be used to control the relative boosting of the high and low intensity components of the signal. It is fair to assume that the energy peaks corresponding to the primary heart sounds will be larger compared to that of murmurs. Under this assumption, by choosing $k_1 > 1$ and $k_2 = 1$, we can boost the primary heart sounds without affecting the intensity of the low amplitude regions. FIG. 3 and FIG. 4 show the effect of boosting the primary heart sounds.

FIG. 3 is an embodiment of an input signal before boosting. FIG. 4 is an embodiment depicting process signal, after a boost, with $k_1=100$ and $k_2=1$. As shown in FIG. 3 and FIG. 4, S1 and S2 locations are boosted while the murmur is not affected. On the other hand, by choosing $k_2 > 1$, thus, boosting the low amplitude regions.

For a dynamic range compression, by controlling the parameters $k_1$ and $k_2$, a dynamic range compression may be provided. The algorithm could be used to provide gain and range compression while recording using a stethoscope as well as provide the noise suppression functionality. The parameters $k_1$ and $k_2$ may either be set by a user, for example, by means of dials on the stethoscope, or by the algorithm based on a rough estimate of the ambient noise and available dynamic range.

As such, the gain adaptation may be used to provide noise robustness and may be formulated to have a Wiener gain like effect. However, the gain provided by Stethoscope method and apparatus may depend on both the SNR and the relative strength of the signal. Thus, such a method may also be used to boost the signal in clean conditions as well as to suppress noise in low SNR conditions.

Figure 5:
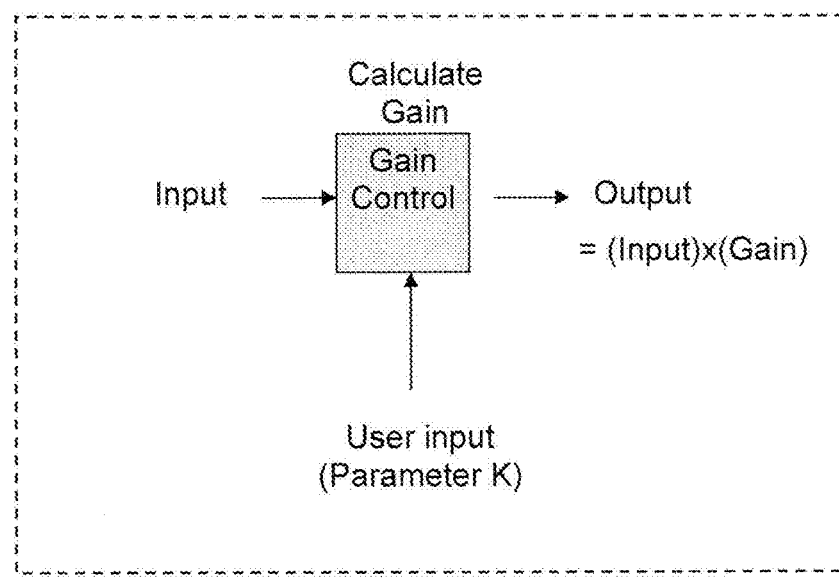
FIG. 5 is an embodiment of an adaptive gain control (AGC) unit.

FIG. 5 is an embodiment of an adaptive gain control (AGC) unit. In this embodiment, the AGC Unit comprises a gain control that provides a simple way for a user to either use the stethoscope in 'noise suppression' mode or in 'amplification' mode. In a noisy environment the user sets a parameter 'K' to less than 1, wherein 1 is the selected threshold. More the noise, lower is the value of 'K'. In a clean environment (if the user desires amplification of low amplitude portions of the signal) she/he sets the value of K greater than 1, wherein 1 is the selected threshold.

The gain control takes in a segment of the input, such as, a window of 1-2 seconds and extracts the amplitude envelope of the signal and calculates the gain to be applied based on a user input ('K') and the relative amplitude of the signal, relative to the maximum of the window. This gain is then multiplied to the signal.

Figure 6:
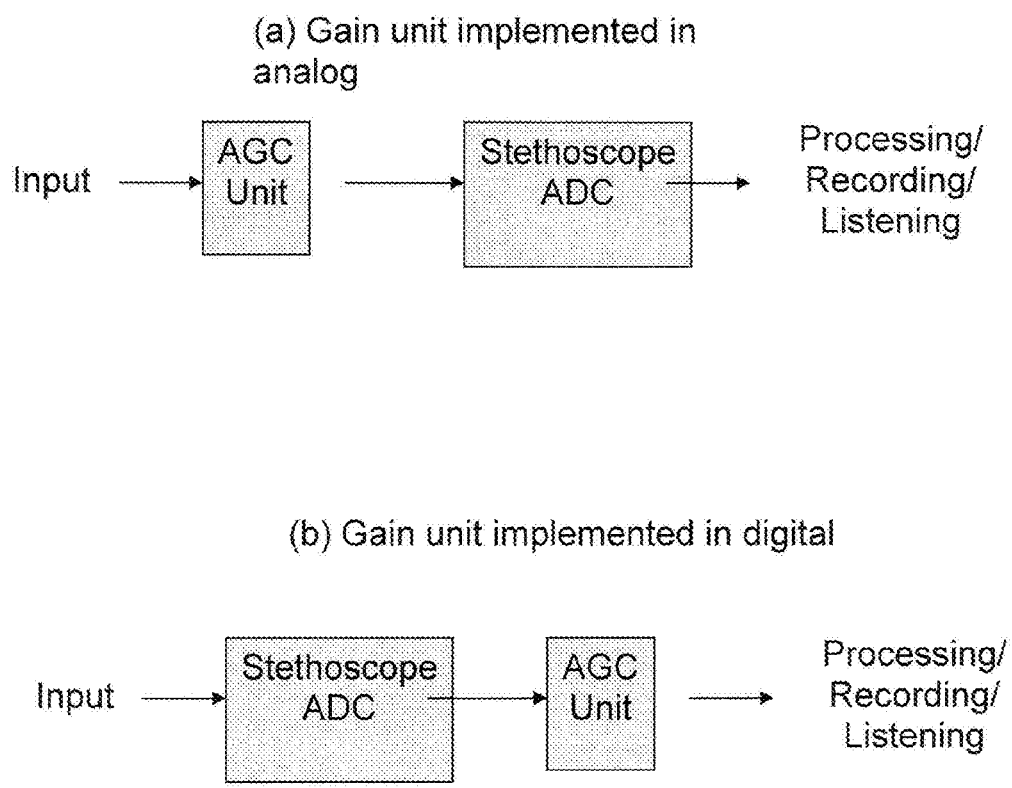
FIGS. 6 (*a*) and (*b*) are embodiments of gain units implements in analog and digital, respectively.

As shown in FIG. 6(a) and (b), the gain unit can be implemented in analog or digital. As shown in 6(a), when implemented in analog, the AGC Unit receives the input and outputs to an ADC of a stethoscope. The stethoscope utilizes the output of the AGC Unit and outputs a signal that can be processed, recorded and/or listened to. As shown in 6(b), when implemented in the digital domain, the ADC of the stethoscope receives the input and outputs to an AGC Unit. The AGC Unit utilizes the output of the stethoscope's ADC and outputs a signal that can be processed, recorded and/or listened to.

Figure 7:
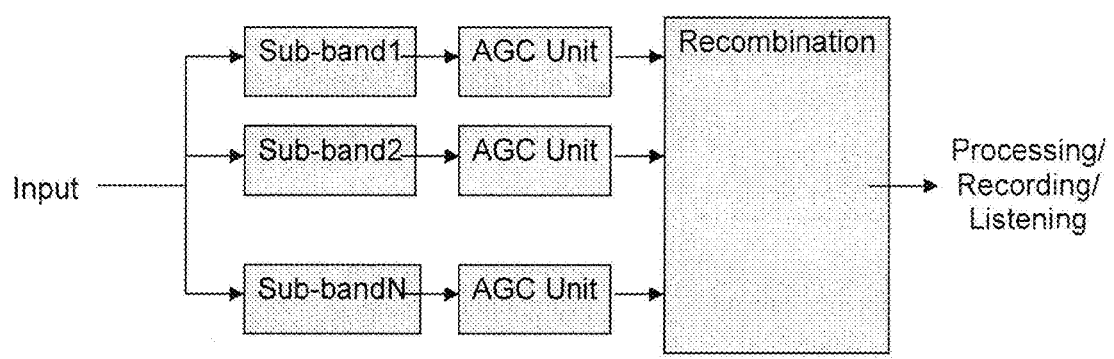
FIG. 7 is an embodiment of adaptive gain control (AGC) units implemented in frequency sub-band.

FIG. 7 is an embodiment of adaptive gain control (AGC) units implemented using frequency sub-bands. The signal is decomposed to different frequency bands and the above step is repeated for each of the sub-bands. The sub-band signals are then recombined to form the output. The gain adaptation can either be done in analog or digital domain based on the front-end being used.

While the foregoing is directed to embodiments of the present invention, other and further embodiments of the invention may be devised without departing from the basic scope thereof, and the scope thereof is determined by the claims that follow.

What is claimed is:

1. An adaptive gain control (AGC) unit of a digital processor, comprising: a gain control for receiving a noisy input signal and determining, via the digital processor, to utilize a stethoscope in at least one of a noise suppression mode or in amplification mode depending if the noise level is at least one of above or below a threshold, wherein the stethoscope is in noise suppression mode when K is less than the threshold and is amplification mode when K is above the threshold, wherein K is a positive scaling factor utilized to control the relative boosting of the high and low intensity components of the input signal.

2. The AGC unit of claim 1, wherein a threshold is selected by a user.

3. The AGC unit of claim 1, wherein the AGC unit is utilized in at least one of an analog, digital or frequency sub-band, wherein the frequency sub-band is at least one of digital or analog.

4. A method of an adaptive gain control (AGC) unit of a digital processor, comprising: receiving a noisy input signal; and determining, via the digital processor, to utilize a stethoscope in at least one of a noise suppression mode or in amplification mode depending if the noise level is at least one of above or below a threshold, wherein the stethoscope is in noise suppression mode when K is less than the threshold and is amplification mode when K is above the threshold, wherein K is a positive scaling factor utilized to control the relative boosting of the high and low intensity components of the input signal.

5. The method of claim 4, wherein a threshold is selected by a user.

6. The method of claim 4, wherein the AGC unit is utilized in at least one of an analog, digital or frequency sub-band, wherein the frequency sub-band is at least one of digital or analog.

7. A non-transitory computer readable medium comprising computer instructions that, when executed by a processor, causes the processor to perform a method, the method comprising: receiving a noisy input signal; and
    determining to utilize a stethoscope in at least one of a noise suppression mode or in amplification mode depending if the noise level is at least one of above or below a threshold, wherein the stethoscope is in noise suppression mode when K is less than the threshold and is amplification mode when K is above the threshold, wherein K is a positive scaling factor utilized to control the relative boosting of the high and low intensity components of the input signal.

8. The computer readable medium of claim 7, wherein the threshold is selected by a user.

9. The computer readable medium of claim 7, wherein the AGC unit is utilized in at least one of an analog, digital or frequency sub-band, wherein the frequency sub-band is at least one of digital or analog.

* * * * *